US012502499B2

(12) United States Patent
Pyeon

(10) Patent No.: US 12,502,499 B2
(45) Date of Patent: Dec. 23, 2025

(54) ANESTHETIC GAS DISTRIBUTION DEVICE

(71) Applicant: VIEWORKS CO., LTD., Anyang-si (KR)

(72) Inventor: Yeong Hyeon Pyeon, Anyang-si (KR)

(73) Assignee: VIEWORKS CO., LTD., Anyang-si (KR)

( * ) Notice: Subject to any disclaimer, the term of this patent is extended or adjusted under 35 U.S.C. 154(b) by 967 days.

(21) Appl. No.: 17/684,662

(22) Filed: Mar. 2, 2022

(65) Prior Publication Data

US 2022/0280735 A1 Sep. 8, 2022

(30) Foreign Application Priority Data

Mar. 2, 2021 (KR) ........................ 10-2021-0027317

(51) Int. Cl.
*A61M 16/01* (2006.01)
*A61M 16/08* (2006.01)

(52) U.S. Cl.
CPC ........ *A61M 16/01* (2013.01); *A61M 16/0891* (2014.02); *A61M 2202/0241* (2013.01); *A61M 2205/3331* (2013.01)

(58) Field of Classification Search
CPC ....... A61D 7/00; A61D 7/04; A61M 16/0891; A61M 16/0816; A61M 16/01; A61M 2202/0241; A61M 2205/3331; A61M 16/104; A61M 16/186; A61M 16/0006; A61M 2250/00; A61M 2205/08; A61M 2205/84; A61M 16/0666; A61M 15/00; A61M 16/0605; A61M 16/0833; F16K 27/00; F16K 27/02; A61B 2205/00
See application file for complete search history.

(56) References Cited

U.S. PATENT DOCUMENTS 4,422,456 A * 12/1983 Tiep .................. A61M 16/0666 128/207.18
5,062,419 A * 11/1991 Rider ................ A61M 16/0833 128/200.14

(Continued)

FOREIGN PATENT DOCUMENTS

CN 101821009 A 9/2010
CN 102512195 A 6/2012

(Continued)

OTHER PUBLICATIONS

Machine Translation of JP2006288560 Specification (Year: 2025).*

(Continued)

*Primary Examiner* — Brandy S Lee
*Assistant Examiner* — Abigayle Dale
(74) *Attorney, Agent, or Firm* — Rabin & Berdo, P.C.

(57) ABSTRACT

Disclosed is an anesthetic gas distribution device capable of being easily adjusted to conform to various conditions of a sample. An anesthetic gas distribution device according to an embodiment of the present invention includes a manifold block including a main block and one or more sub-blocks coupled to one side or two opposite sides of the main block so as to be separable in a first direction, the manifold block being configured to be supplied with the gas from the outside, and supply nozzles connected to the manifold block in a second direction perpendicular to the first direction and configured to supply the gas to the sample.

13 Claims, 7 Drawing Sheets

(56) References Cited

U.S. PATENT DOCUMENTS

| | | | | | |
|---|---|---|---|---|---|
| 5,297,502 | A * | 3/1994 | Jaeger | A61D 7/04 | 119/420 |
| 7,464,707 | B2 * | 12/2008 | Dalgetty | A61D 7/04 | 128/203.15 |
| 2003/0154976 | A1 | 8/2003 | Dalgetty et al. | | |
| 2009/0050151 | A1 * | 2/2009 | Fuhrman | A61M 16/0084 | 128/205.12 |
| 2012/0216807 | A1 | 8/2012 | Dunlop | | |
| 2015/0047724 | A1 | 2/2015 | Leevy et al. | | |
| 2017/0312066 | A1 * | 11/2017 | Leevy | A61G 10/00 | |
| 2020/0038163 | A1 * | 2/2020 | Tse | A61D 3/00 | |

FOREIGN PATENT DOCUMENTS

| | | | | |
|---|---|---|---|---|
| CN | 103028174 | A | 4/2013 | |
| CN | 107654780 | A | 2/2018 | |
| CN | 109069778 | A | 12/2018 | |
| JP | 2006288560 | A * | 10/2006 | A61D 7/04 |
| JP | 2008089085 | A | 4/2008 | |
| JP | 2018017245 | A | 2/2018 | |
| KR | 20180011736 | A | 2/2018 | |

OTHER PUBLICATIONS

JP 2006/288560 A Specification Machine Translation (Year: 2025).*

The State Intellectual Property Office of People's Republic of China First Office Action, Application No. 202210193824, dated Jun. 7, 2024.

* cited by examiner

ANESTHETIC GAS DISTRIBUTION DEVICE

CROSS-REFERENCE TO RELATED APPLICATIONS

This application claims priority to and the benefit of Korean Patent Application No. 10-2021-0027317 filed in the Korean Intellectual Property Office on Mar. 2, 2021, the entire contents of which are incorporated herein by reference.

TECHNICAL FIELD

The present invention relates to an anesthetic gas distribution device, and more particularly, to an anesthetic gas distribution device in which a plurality of blocks provided in a manifold block is organized into a module.

BACKGROUND ART

Inhalation anesthesia tends to be mainly used to anesthetize experimental animals for surgery, drug administration, tissue collection, and image capturing to be performed on animals.

In the case of an anesthetic gas manifold in the related art, because the number of gas discharge ports for each manifold or a position of the gas discharge port is fixed, the number of samples (experimental animals) or the position of the sample needs to conform to the specifications of the manifold. For this reason, there is a problem in that the number of samples increases and the anesthetic gas manifold in the related art has a limitation in supplying anesthetic gas to a large-sized sample.

DOCUMENT OF RELATED ART

Patent Document (Patent Document 1) U.S. Patent Publication No. 2015-0047724

SUMMARY OF THE INVENTION

The present invention has been made in an effort to provide an anesthetic gas distribution device capable of appropriately supplying anesthetic gas according to the number of samples and a size of the sample.

Specifically, the present invention has been made in an effort to provide an anesthetic gas distribution device in which a plurality of blocks provided in a manifold block is organized into a module, which makes it possible to easily assemble and disassemble the anesthetic gas distribution device according to a user's necessity.

The present invention has also been made in an effort to provide an anesthetic gas distribution device capable of being easily adjusted to conform to various conditions of samples.

An exemplary embodiment of the present invention provides an anesthetic gas distribution device, which is configured to supply gas to a sample, including: a manifold block including a main block and one or more sub-blocks coupled to one side or two opposite sides of the main block so as to be separable in a first direction, the manifold block being configured to be supplied with the gas from the outside; and supply nozzles connected to the manifold block in a second direction perpendicular to the first direction and configured to supply the gas to the sample.

The anesthetic gas distribution device may further include passageway portions respectively provided in the main block and the sub-block such that the gas supplied from the outside passes through the passageway portions.

The anesthetic gas distribution device may further include a sliding unit provided in the passageway portion of the sub-block and configured to move in the first direction in the sub-block along the passageway portion of the sub-block.

The anesthetic gas distribution device may further include: a first connection unit configured to connect the passageway portion of the main block and the sliding unit in the sub-block; and a second connection unit configured to connect the neighboring sliding units in the sub-blocks.

The first connection unit may include: a first flow tube provided in the first connection unit and inserted into the sliding unit; an insertion portion protruding in a diameter direction from an outer periphery of the first flow tube and coupled to the passageway portion of the main block in the first direction; and a first enlarged diameter portion having a larger diameter than the first flow tube and the insertion portion, connected to the insertion portion, and protruding in the diameter direction from the outer periphery of the first flow tube, and the first enlarged diameter portion may be seated in a first groove portion formed in the passageway portion of the sub-block.

The second connection unit may include: a second flow tube provided in the second connection unit and configured to connect the two neighboring sliding units; and a second enlarged diameter portion having a larger diameter than the second flow tube and protruding in a diameter direction from an outer periphery of the second flow tube, and the second enlarged diameter portion may be seated in first groove portions formed in the passageway portions of the adjacent sub-blocks.

The supply nozzles may include: a first supply nozzle coupled to the passageway portion of the main block; and a second supply nozzle coupled to the sliding unit and configured to move together with the sliding unit when the sliding unit moves in the first direction, and the sliding unit may be movable in a space between the first connection unit and the second connection unit based on the first direction or a space between the second connection units adjacent to each other in the first direction.

The passageway portion of the sub-block may further include a second groove portion formed at a lateral side of the sub-block based on the second direction and configured to define a space in which the second supply nozzle moves in the first direction.

The main block may further include a gas inlet port connected to the passageway portion of the main block and configured to receive the gas from the outside.

The anesthetic gas distribution device may further include residual gas flow portions respectively provided in the main block and the sub-block and disposed at positions spaced apart from the passageway portions in the second direction, and the gas, which remains after a process of supplying the gas to the sample, may flow through the residual gas flow portions.

The anesthetic gas distribution device may further include intake ports respectively provided in the main block and the sub-block and connected to the residual gas flow portions in the second direction, and the gas, which remains after the process of supplying the gas to the sample, may flow into the residual gas flow portions through the intake ports.

The anesthetic gas distribution device may further include third connection units configured to connect the residual gas flow portion of the main block and the residual gas flow portion of the sub-block and connect the residual gas flow portions of the sub-blocks.

The third connection unit may include a third flow tube provided in the third connection unit, and the gas, which is introduced into the residual gas flow portion of the sub-block, may flow through the third flow tube.

The main block may further include a gas outlet port connected to the residual gas flow portion of the main block and configured to discharge the gas, which flows in the residual gas flow portions of the main block and the sub-block, to the outside.

The anesthetic gas distribution device may further include a first cover coupled to the passageway portion of the sub-block positioned at an outermost position from the main block among the sub-blocks.

The anesthetic gas distribution device may further include a second cover coupled to the residual gas flow portion of the sub-block positioned at the outermost position from the main block among the sub-blocks.

The anesthetic gas distribution device may further include sealing members coupled to sealing member accommodation portions provided on the sliding unit and configured to seal a gap between the first connection unit and the sliding unit and a gap between the second connection unit and the sliding unit.

According to the present invention, it is possible to provide an anesthetic gas distribution device in which the plurality of blocks provided in the manifold block is organized into the module, such that the block may be added according to the number of samples, and the anesthetic gas distribution device may be easily assembled and disassembled according to the use or necessity of the user.

It is possible to easily adjust the position of the supply nozzle according to various conditions of the samples (sizes and positions of samples and intervals between samples).

The foregoing summary is illustrative only and is not intended to be in any way limiting. In addition to the illustrative aspects, embodiments, and features described above, further aspects, embodiments, and features will become apparent by reference to the drawings and the following detailed description.

Figure 1:
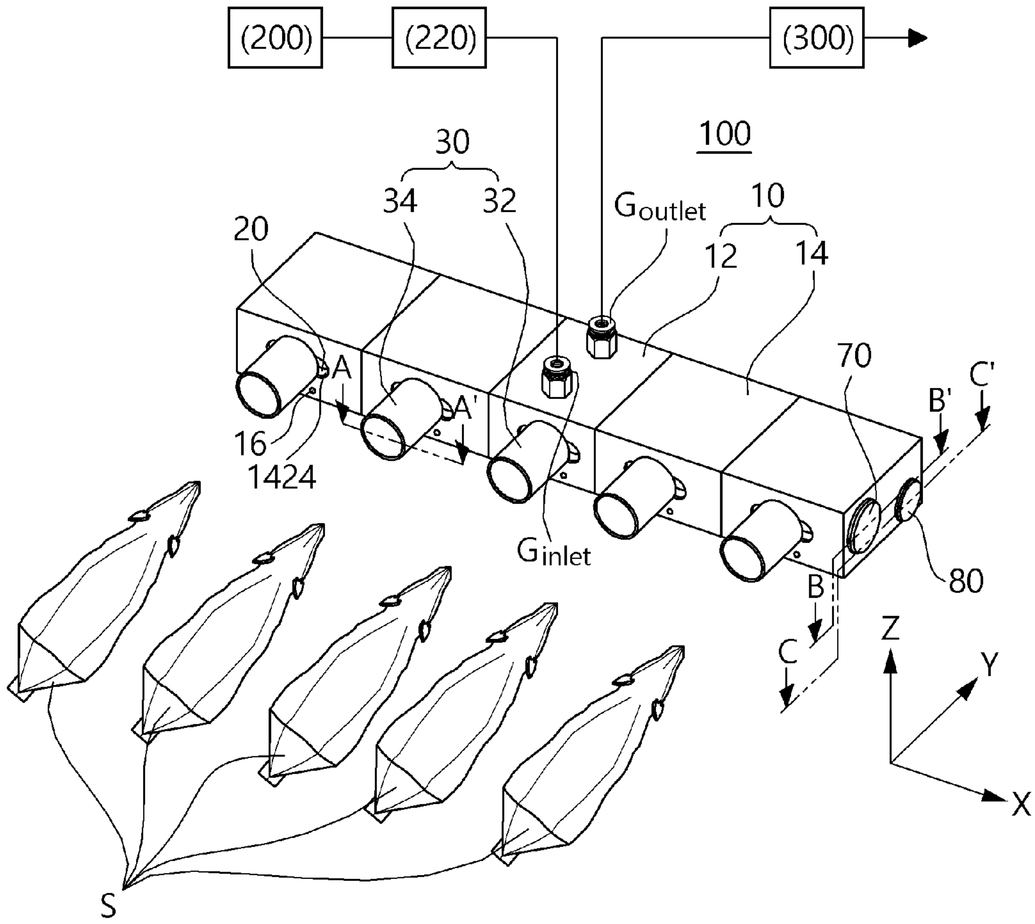
FIG. 1 is a view illustrating an overall shape of an anesthetic gas distribution device according to an embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings. First, in assigning reference numerals to constituent elements of the respective drawings, it should be noted that the same constituent elements will be designated by the same reference numerals, if possible, even though the constituent elements are illustrated in different drawings. In addition, in the description of the present invention, the specific descriptions of publicly known related configurations or functions will be omitted when it is determined that the specific descriptions may obscure the subject matter of the present invention. Further, the exemplary embodiments of the present invention will be described below, but the technical spirit of the present invention is not limited thereto and may of course be modified and variously carried out by those skilled in the art.

Figure 2:
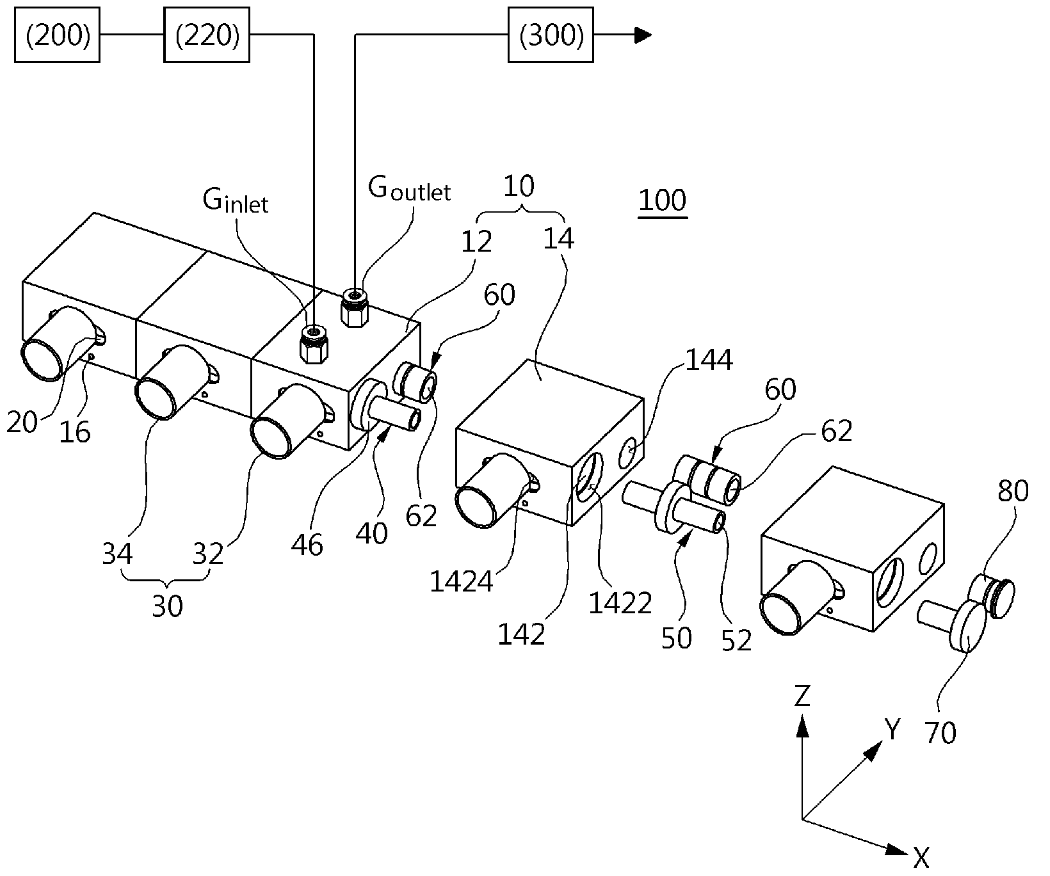
FIG. 2 is a view illustrating a state in which a part of the anesthetic gas distribution device according to the embodiment of the present invention is disassembled.
Figure 3:
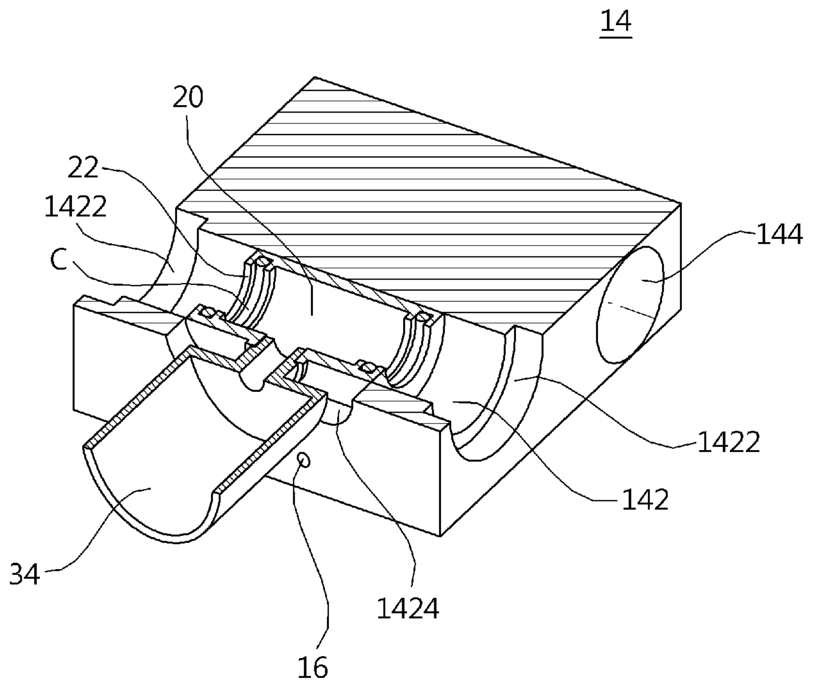
FIG. 3 is a view illustrating an internal structure of a sub-block of a manifold block (a cross-section taken along line A-A' in FIG. 1).
Figure 4:
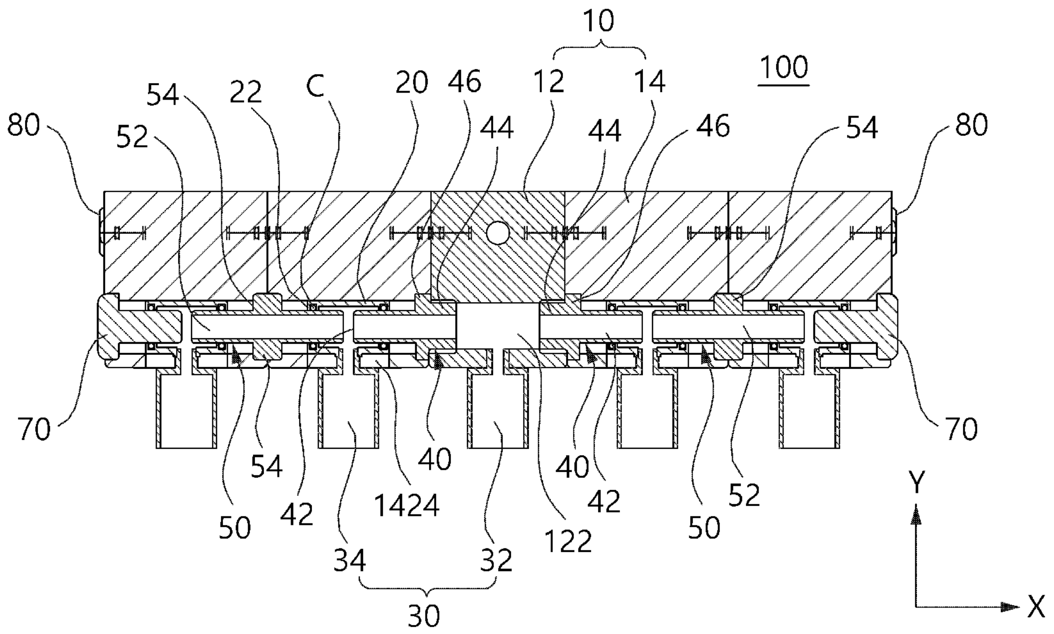
FIG. 4 is a view illustrating a detailed structure of the anesthetic gas distribution device according to the present invention (a cross-section taken along line B-B' in FIG. 1).
Figure 5:
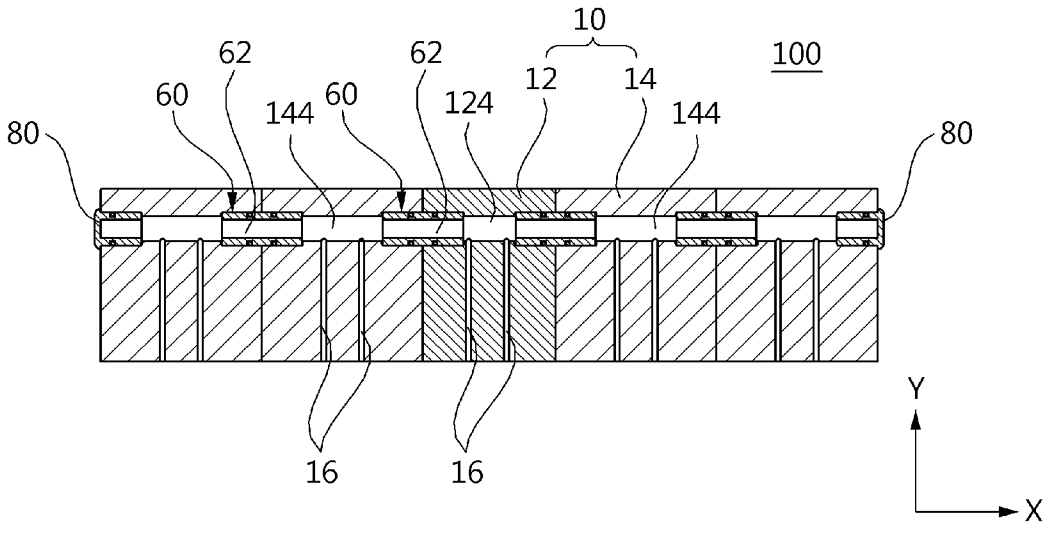
FIG. 5 is a view illustrating a detailed structure of the anesthetic gas distribution device according to the present invention (a cross-section taken along line C-C' in FIG. 1).

FIG. 1 is a view illustrating an overall shape of an anesthetic gas distribution device 100 according to an embodiment of the present invention, FIG. 2 is a view illustrating a state in which a part of the anesthetic gas distribution device 100 according to the embodiment of the present invention is disassembled, FIG. 3 is a view illustrating an internal structure of a sub-block 14 of a manifold block 10 (a cross-section taken along line A-A' in FIG. 1), FIG. 4 is a view illustrating a detailed structure of the anesthetic gas distribution device 100 according to the present invention (a cross-section taken along line B-B' in FIG. 1), and FIG. 5 is a view illustrating a detailed structure of the anesthetic gas distribution device 100 according to the present invention (a cross-section taken along line C-C' in FIG. 1). In this case, an external gas supply source 200, a supply pump 220, a discharge pump 300, and a sample S, which will be described below with reference to cross-sectional views of FIGS. 4 and 5, are not illustrated in these drawings.

Hereinafter, in the embodiment of the present invention, a first direction is defined as an X-axis direction, a second direction perpendicular to the first direction is defined as a Y-axis direction, and a direction perpendicular to both the first direction and the second direction is defined as a Z-axis direction.

Referring to FIGS. 1 and 2, the anesthetic gas distribution device 100 according to the embodiment of the present invention may include the manifold block 10 including a main block 12 and one or more sub-blocks 14 coupled to the main block 12.

The main block 12 of the manifold block 10 includes a gas inlet port $G_{inlet}$ through which gas is supplied from the external gas supply source 200, and a gas outlet port $G_{outlet}$ through which the gas is discharged to the outside. For example, the gas may be an anesthetic gas to be supplied to the sample S.

In this case, the supply pump 220 may be provided between the external gas supply source 200 and the gas inlet port $G_{inlet}$ and provide pumping power so that the gas in the external gas supply source 200 may be supplied to the main block 12 and the sub-blocks 14 through the gas inlet port $G_{inlet}$.

One or more sub-blocks 14 may be provided, and the sub-blocks 14 may be coupled to one side or two opposite sides of the main block 12 so as to be separable in the first direction.

Referring to FIGS. 1 to 4, the main block 12 and the sub-block 14 may have passageway portions 122 and 142, respectively, and the gas supplied from the external gas supply source 200 through the gas inlet port $G_{inlet}$ may pass through the passageway portions 122 and 142. In this case, the gas inlet port $G_{inlet}$ may be connected to the passageway portion 122 of the main block 12.

A sliding unit 20 may be provided in the passageway portion 142 of the sub-block 14, and the sliding unit 20 may move in the sub-block 14 in the first direction along the passageway portion 142 of the sub-block 14. In this case, the sliding unit 20 may have, but not limited to, a hollow cylindrical shape corresponding to a shape of the passageway portion 142.

Meanwhile, the anesthetic gas distribution device 100 according to the present invention further includes supply nozzles 30. For example, the supply nozzle 30 may be connected to the manifold block 10 in the second direction perpendicular to the first direction and supply the gas to the sample S.

In more detail, the supply nozzle 30 may be coupled to the passageway portion 122 of the main block 12 and the sliding unit 20 in the second direction perpendicular to the first direction. The supply nozzle 30 may supply the sample S with the gas which is supplied to the passageway portion 122 of the main block 12 or supplied to the passageway portion 142 of the sub-block 14 through the gas inlet port $G_{inlet}$.

As illustrated in FIG. 1, the sample S may be fixed at a position corresponding to the supply nozzle 30 and fixed by a separate fixing device (not illustrated). For example, the sample S may be, but not limited to, a small animal such as a rodent.

Referring to FIG. 1 to FIGS. 3 and 5, the main block 12 and the sub-block 14 may have residual gas flow portions 124 and 144, respectively, therein. The residual gas flow portion 124 or 144 may be positioned at a position spaced apart from the passageway portion 122 or 142 in the second direction. The gas, which remains after a process of supplying the gas to the sample S, may flow through the residual gas flow portion 124 or 144. However, the residual gas flow portion 124 or 144 need not be necessarily spaced apart from the passageway portion 122 or 142, and the residual gas flow portion 124 or 144 may be disposed adjacent to the passageway portion 122 or 142 in the second direction.

The main block 12 and the sub-block 14 may have intake ports 16, respectively. The intake port 16 may be connected to the residual gas flow portion 124 or 144 in the second direction. For example, the gas, which remains after the process of supplying the gas to the sample S, may flow into the residual gas flow portion 124 or 144 through the intake port 16.

In this case, the discharge pump 300 may be provided between the gas outlet port $G_{outlet}$ and the outside and provide pumping power so that the residual gas flowing in the residual gas flow portions 124 and 144 may be discharged to the outside.

In the embodiment of the present invention, the anesthetic gas distribution device 100 and the sample S may be positioned in a separate hermetic chamber (not illustrated).

Referring to FIGS. 2 to 4, the anesthetic gas distribution device 100 may further include first connection units 40 and second connection units 50.

In detail, the passageway portion 122 of the main block 12 and the sliding unit 20 in the sub-block 14 may be connected by the first connection unit 40, and the sliding units 20 in the adjacent sub-blocks 14 may be connected by the second connection unit 50.

For example, each of the first and second connection units 40 and 50 may have a hollow shape. The gas, which is supplied to the passageway portions 122 and 142 through the gas inlet port $G_{inlet}$ may be supplied to the sample S through the supply nozzles 30 while flowing in the first direction through the interior of the first connection unit 40, the interior of the sliding unit 20, and the interior of the second connection unit 50.

In more detail, the first connection unit 40 includes a first flow tube 42 having therein a passageway through which the gas supplied to the passageway portion 122 of the main block 12 flows, an insertion portion 44 having a larger diameter than the first flow tube 42 and coupled to the passageway portion 122 of the main block 12 in the first direction, and a first enlarged diameter portion 46 having a larger diameter than the first flow tube 42 and the insertion portion 44, connected to the insertion portion 44, and seated in a first groove portion 1422 formed in the passageway portion 142 of the sub-block 14 which will be described below. In this case, the first flow tube 42 may be inserted into the sliding unit 20. The insertion portion 44 and the first enlarged diameter portion 46 may protrude from an outer periphery of the first flow tube 42 in a diameter direction.

The second connection unit 50 includes a second flow tube 52 having therein a passageway through which the gas supplied through the first connection unit 40 and the sliding unit 20 flows, and a second enlarged diameter portion 54 having a larger diameter than the second flow tube 52 and seated in the first groove portion 1422 formed in the passageway portion 142 of the sub-block 14. In this case, one side of the second flow tube 52 based on the second enlarged diameter portion 54 may be inserted into one of the sliding units 20, and the other side of the second flow tube 52 based on the second enlarged diameter portion 54 may be inserted into the other of the sliding units 20. In addition, the second enlarged diameter portion 54 of the second connection unit 50 may be seated in the first groove portions 1422 formed in the passageway portions 142 of the different sub-blocks 14. The second enlarged diameter portion 54 may protrude from an outer periphery of the second flow tube 52 in the diameter direction.

Meanwhile, as illustrated in FIGS. 2 and 4, the first connection unit 40 may be formed to be asymmetric in the first direction with respect to the first enlarged diameter portion 46, but the present invention is not limited thereto.

As illustrated in FIGS. 2 and 4, the second connection unit 50 may be formed to be symmetric in the first direction with respect to the second enlarged diameter portion 54, but the present invention is not limited thereto.

Referring to FIGS. 2, 3, and 5, the anesthetic gas distribution device 100 further includes third connection units 60.

The residual gas flow portion 124 of the main block 12 and the residual gas flow portion 144 of the sub-block 14 may be connected by the third connection unit 60, and the residual gas flow portions 144 of the sub-blocks 14 may be connected by the third connection unit 60.

For example, the third connection unit 60 may have a hollow shape. The gas, which is introduced into the residual gas flow portion 144 of the sub-block 14 through the intake port 16 of the sub-block 14, may flow through the third connection unit 60 and be discharged through the gas outlet port $G_{outlet}$.

In more detail, the third connection unit 60 includes a third flow tube 62 having a passageway through which the gas introduced into the residual gas flow portion 144 of the sub-block 14 flows. The gas, which is introduced into the residual gas flow portion 144 of the sub-block 14, may flow into the residual gas flow portion 124 of the main block 12 through the third flow tube 62 and then be discharged through the gas outlet port $G_{outlet}$.

Referring to FIGS. 1 to 4, the supply nozzles 30 include a first supply nozzle 32 coupled to the passageway portion 122 of the main block 12, and a second supply nozzle 34 coupled to the sliding unit 20 and configured to move together with the sliding unit 20 when the sliding unit 20 moves in the first direction.

Meanwhile, the passageway portion 142 of the sub-block 14 includes the first groove portions 1422 in which the first enlarged diameter portion 46 of the first connection unit 40 and the second enlarged diameter portion 54 of the second connection unit 50 are seated, and a second groove portion 1424 configured to define a space in which the second supply nozzle 34 moves in the first direction.

For example, as illustrated in FIGS. 3 and 4, the first groove portions 1422 may be formed at lateral sides of the sub-block 14 based on the first direction. The first groove portion 1422 may have a larger diameter than a space of the passageway portion 142 of the sub-block 14 in which the sliding unit 20 is disposed. The first enlarged diameter portion 46 of the first connection unit 40 and the second enlarged diameter portion 54 of the second connection unit 50 are seated in the first groove portions 1422, which makes it possible to prevent the sliding unit 20 from separating from the passageway portion 142 of the sub-block 14 when the sliding unit 20 moves in the first direction.

As illustrated in FIGS. 1 to 4, the second groove portion 1424 may be formed at a lateral side of the sub-block 14 based on the second direction. For example, the second groove portion 1424 may be provided in the form of a long hole formed in the first direction, thereby defining the space in which the second supply nozzle 34 moves in the first direction as the sliding unit 20 moves in the first direction.

Referring to FIGS. 1, 2, 4, and 5, the anesthetic gas distribution device 100 further includes first covers 70 coupled to the passageway portions 142 of the sub-blocks 14 positioned at outermost positions from the main block 12 among the sub-blocks 14, and second covers 80 coupled to the residual gas flow portions 144 of the sub-blocks 14 positioned at the outermost positions from the main block 12 among the sub-blocks 14.

Particularly, the first covers 70 may prevent the gas, which is supplied to the passageway portions 122 and 142 from the gas inlet port $G_{inlet}$, from leaking to the outside (prevent the supplied gas from leaking in the first direction).

The second covers 80 may prevent the residual gas, which is recovered and flows in the residual gas flow portions 124 and 144 of the main block 12 and the sub-block 14, from leaking to the outside (prevent the recovered gas from leaking in the first direction), which makes it possible to discharge the whole amount of gas to the outside through the gas outlet port $G_{outlet}$.

Referring to FIGS. 3 and 4, the anesthetic gas distribution device 100 further includes sealing members C coupled to sealing member accommodation portions 22 provided on the sliding unit 20 and configured to seal a gap between the first connection unit 40 and the sliding unit 20 and a gap between the second connection unit 50 and the sliding unit 20.

In more detail, the sealing member C may seal a gap between the sliding unit 20 and the first flow tube 42 of the first connection unit 40 and a gap between the sliding unit 20 and the second flow tube 52 of the second connection unit 50.

Meanwhile, the sealing member accommodation portion 22 may be formed along an inner peripheral surface of the sliding unit 20, and the sealing member C may be made of a material excellent in waterproofness and wear resistance.

Figure 6:
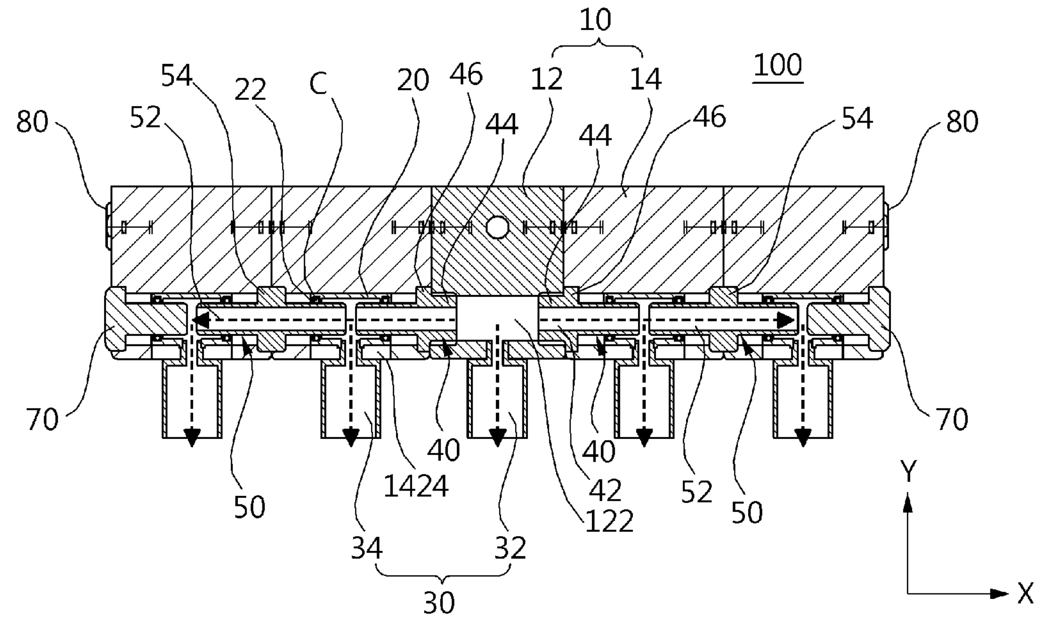
FIG. 6 is a view illustrating a flow of gas in the anesthetic gas distribution device according to the present invention at the time of supplying gas to a sample.

FIG. 6 is a view illustrating a flow of gas in the anesthetic gas distribution device 100 according to the present invention at the time of supplying the gas to the sample S.

Referring to FIGS. 1, 2, and 6, in the anesthetic gas distribution device 100 according to the present invention, the gas, which is supplied into the passageway portion 122 of the main block 12 through the gas inlet port $G_{inlet}$ connected to the passageway portion 122 of the main block 12, may be discharged to the outside through the first supply nozzle 32 or pass through the passageway portion 142 of the sub-block 14 while flowing through the first flow tube 42 of the first connection unit 40, the sliding unit 20, and the second flow tube 52 of the second connection unit 50 and then be discharged to the outside through the second supply nozzle 34.

In this case, the first cover 70 may prevent the gas, which is supplied to the passageway portions 122 and 142 from the gas inlet port $G_{inlet}$, from leaking to the outside in the first direction, which makes it possible to supply the whole amount of gas to the sample S through the supply nozzle 30.

According to the embodiment of the present invention, it is possible to provide the anesthetic gas distribution device 100 in which the plurality of blocks provided in the manifold block 10 is organized into the module, such that the sub-block 14 may be added coupled to the number of samples S, and the anesthetic gas distribution device 100 may be easily assembled and disassembled according to the user's necessity.

Meanwhile, in the embodiment of the present invention, the manifold block 10 is illustrated as having the configuration in which the two sub-blocks 14 are provided at each of the two opposite sides of the single main block 12, but the present invention is not limited thereto. A single sub-block 14 may be provided at one side of the main block 12 or three or more sub-blocks 14 may be additionally provided at each of the two opposite sides of the main block 12 according to the number of samples S.

Figure 7:
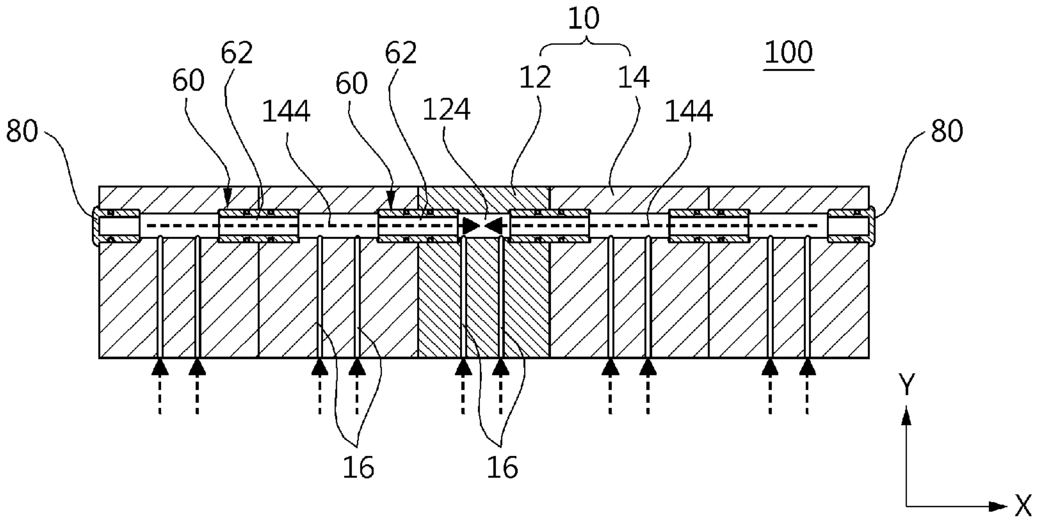
FIG. 7 is a view illustrating a flow of gas in the anesthetic gas distribution device according to the present invention at the time of recovering gas.

FIG. 7 is a view illustrating a flow of gas in the anesthetic gas distribution device 100 according to the present invention at the time of recovering the gas.

Referring to FIGS. 1, 2, and 7, the gas, which remains after the process of supplying the gas to the sample S, may flow into the residual gas flow portions 124 and 144 through the intake ports 16 in the anesthetic gas distribution device 100 according to the present invention.

In this case, the gas, which is introduced into the residual gas flow portion 124 of the main block 12 through the intake port 16 of the main block 12, may be discharged immediately to the outside through the gas outlet port $G_{outlet}$.

Meanwhile, the gas, which is introduced into the residual gas flow portion 144 of the sub-block 14 through the intake port 16 of the sub-block 14, may flow toward the residual gas flow portion 124 of the main block 12 through the third flow tube 62 of the third connection unit 60 and then be discharged to the outside through the gas outlet port $G_{outlet}$ connected to the residual gas flow portion 124 of the main block 12.

In this case, the second cover 80 may prevent the residual gas, which is recovered and flows in the residual gas flow portions 124 and 144 of the main block 12 and the sub-block 14, from leaking to the outside in the first direction, which makes it possible to discharge the whole amount of gas to the outside through the gas outlet port $G_{outlet}$.

Figure 8A:
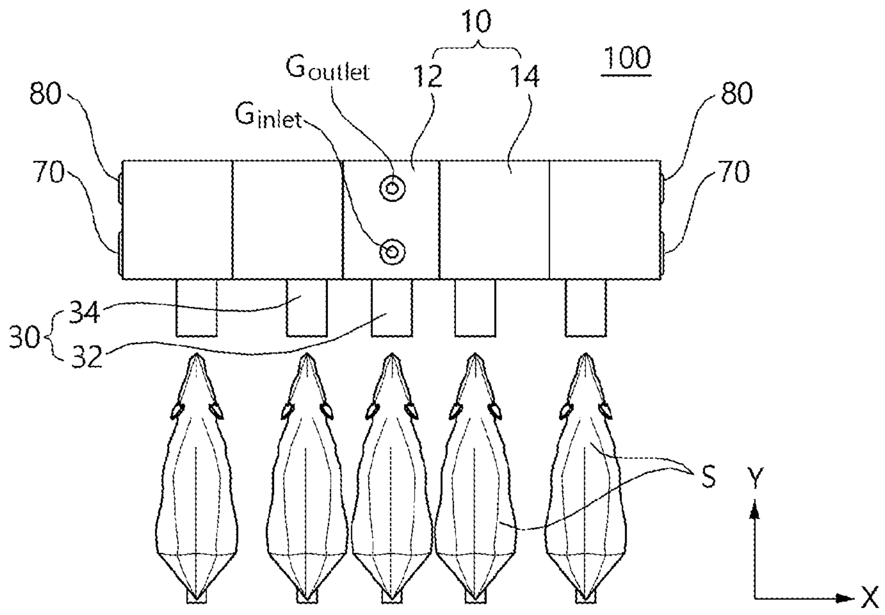
FIGS. 8A and 8B are views illustrating states in which a position of a supply nozzle is changed at the time of assembling the manifold block.
Figure 8B:
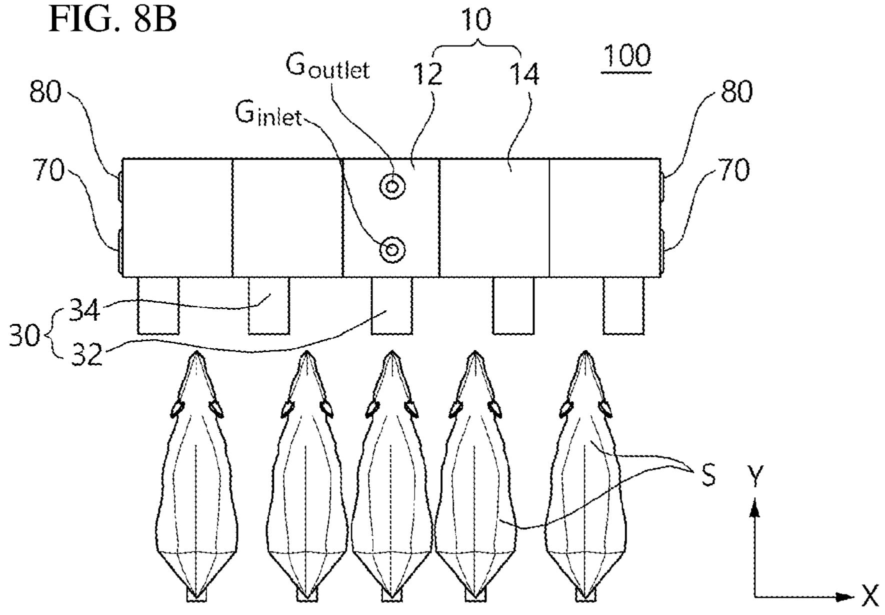
Figure 9A:
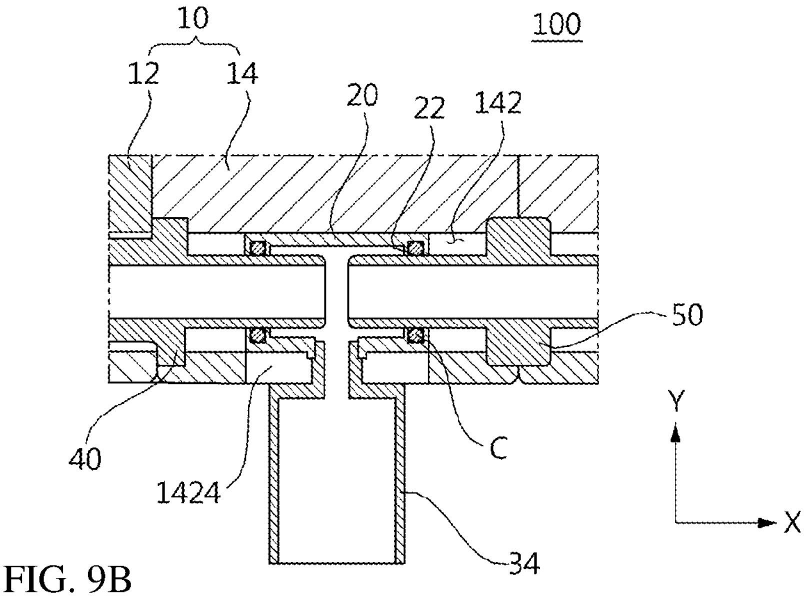
FIGS. 9A and 9B are views illustrating cross-sections indicating states in which a position of the supply nozzle is changed at the time of assembling the manifold block.
Figure 9B:
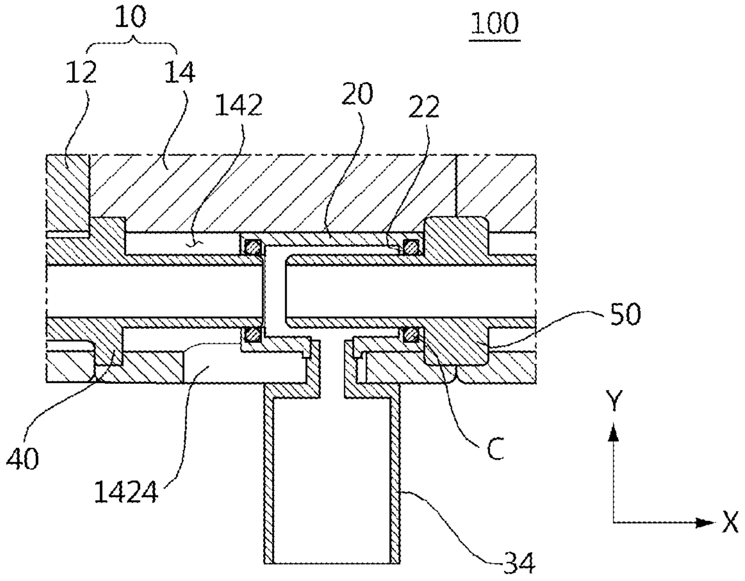

FIGS. 8A and 8B are views illustrating states in which a position of the supply nozzle 30 is changed at the time of assembling the manifold block 10, and FIGS. 9A and 9B are views illustrating cross-sections indicating states in which a position of the supply nozzle 30 is changed at the time of assembling the manifold block 10. In this case, the external gas supply source 200, the supply pump 220, and the discharge pump 300 are not illustrated in FIGS. 8 and 9.

In this case, FIG. 8B is a view illustrating a state before the position of the supply nozzle 30 is changed, and FIG. 8A is a view illustrating a state after the position of the supply nozzle 30 is changed to correspond to the position of the sample S.

Referring to FIGS. 8A, 8B, 9A, and 9B, the first supply nozzle 32, which is coupled to the passageway portion 122 of the main block 12 among the supply nozzles 30, may be kept in a stationary state. However, the first supply nozzle 32 need not be necessarily kept in the stationary state. A separate sliding unit 20 may also be provided in the passageway portion 122 of the main block 12, and the first supply nozzle 32 may be coupled to the sliding unit 20. Therefore, as the sliding unit 20 moves in the first direction in the main block 12, the first supply nozzle 32 may move in the first direction within a range in which the sliding unit 20 is movable.

Meanwhile, the sliding unit 20 may be provided in the passageway portion 142 of the sub-block 14. As illustrated in FIG. 9B, the sliding unit 20 may move in the first direction in the sub-block 14 along the passageway portion 142 of the sub-block 14 from the state illustrated in FIG. 9A.

In this case, the sliding unit 20 may move in the first direction in a space between the first and second connection units 40 and 50 based on the first direction or a space between the second connection units 50 adjacent to each other in the first direction. As the sliding unit 20 moves in the first direction, the second supply nozzle 34 may also move in the first direction within a range in which the sliding unit 20 is movable.

In addition, the sliding unit 20 may move in the first direction in a space between the second connection unit 50 and the first cover 70.

Therefore, the sliding unit 20 does not separate from the space between the first connection unit 40 and the second connection unit 50 based on the first direction or the space between the second connection units 50 based on the first direction, such that the sliding unit 20 may move in the first direction in the sealed space and the internal space of the sliding unit 20 may always maintain a constant gas pressure.

Since the space in the sliding unit 20 always maintains a constant gas pressure as described above, a constant amount of gas may always be supplied through the second supply nozzle 34 regardless of the movement of the sliding unit 20 in the first direction.

According to the embodiment of the present invention, the position of the second supply nozzle 34, among the supply nozzles 30, may be easily adjusted in the first direction according to various conditions of the sample S (sizes and positions of the samples and intervals between the samples). In addition, in the case in which the separate sliding unit 20 is also provided in the passageway portion 122 of the main block 12, the position of the first supply nozzle 32 may also be easily adjusted in the first direction.

The above description is simply given for illustratively describing the technical spirit of the present invention, and those skilled in the art to which the present invention pertains will appreciate that various modifications, changes, and substitutions are possible without departing from the essential characteristic of the present invention. Accordingly, the embodiments disclosed in the present invention and the accompanying drawings are intended not to limit but to describe the technical spirit of the present invention, and the scope of the technical spirit of the present invention is not limited by the embodiments and the accompanying drawings. The protective scope of the present invention should be construed based on the following claims, and all the technical spirit in the equivalent scope thereto should be construed as falling within the scope of the present invention.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An anesthetic gas distribution device, which is configured to supply gas to a sample, comprising:

a manifold block comprising a main block and at least one sub-block coupled to one side or two opposite sides of the main block so as to be separable in a first direction, the manifold block being configured to be supplied with the gas from outside;

supply nozzles connected to the manifold block in a second direction perpendicular to the first direction and configured to supply the gas to the sample;

a first passageway portion and a second passageway portion respectively provided in the main block and the at least one sub-block such that the gas supplied from the outside passes through the first passageway portion and the second passageway portion; and a sliding unit provided in the second passageway portion of the at least one sub-block and configured to move in the first direction in the at least one sub-block along the second passageway portion of the at least one sub-block, a first connection unit configured to connect the first passageway portion of the main block and the sliding unit in the at least one sub-block; and a second connection unit configured to connect neighboring sliding units in a plurality of the at least one sub-block, wherein the supply nozzles comprise:

a first supply nozzle coupled to the first passageway portion of the main block; and a second supply nozzle coupled to the sliding unit and configured to move together with the sliding unit when the sliding unit moves in the first direction, and wherein the sliding unit is movable in a space between the first connection unit and the second connection unit based on the first direction or a space between second connection units adjacent to each other in the first direction.

2. The anesthetic gas distribution device of claim 1, wherein the first connection unit comprises:

a first flow tube provided in the first connection unit and inserted into the sliding unit;

an insertion portion protruding in a diameter direction from an outer periphery of the first flow tube and coupled to the first passageway portion of the main block in the first direction; and a first enlarged diameter portion having a larger diameter than a diameter of the first flow tube and a diameter of the insertion portion, connected to the insertion portion, and protruding from the outer periphery of the first flow tube, and wherein the first enlarged diameter portion is seated in a first groove portion formed in the second passageway portion of the at least one sub-block.

3. The anesthetic gas distribution device of claim 1, wherein the second connection unit comprises:

a second flow tube provided in the second connection unit and configured to connect the neighboring sliding units; and a second enlarged diameter portion having a larger diameter than the second flow tube and protruding from an outer periphery of the second flow tube, and wherein the second enlarged diameter portion is seated in a first groove portion formed in the second passageway portion of the at least one sub-block.

4. The anesthetic gas distribution device of claim 1, wherein the second passageway portion of the at least one sub-block further comprises a second groove portion formed at a lateral side of the at least one sub-block based on the second direction and configured to define a space in which the second supply nozzle moves in the first direction.

5. The anesthetic gas distribution device of claim 1, wherein the main block further comprises a gas inlet port connected to the first passageway portion of the main block and configured to receive the gas from the outside.

6. The anesthetic gas distribution device of claim 1, further comprising:

a first residual gas flow portion and a second residual gas flow portion respectively provided in the main block and the at least one sub-block and disposed at positions spaced apart from the first passageway portion and the second passageway portion in the second direction, wherein the gas, which remains after a process of supplying the gas to the sample, flows through the first residual gas flow portion and the second residual gas flow portion.

7. The anesthetic gas distribution device of claim 6, further comprising:

intake ports respectively provided in the main block and the at least one sub-block and connected to the first residual gas flow portion and the second residual gas flow portion in the second direction, wherein the gas, which remains after the process of supplying the gas to the sample, flows into the first residual gas flow portion and the second residual gas flow portion through the intake ports.

8. The anesthetic gas distribution device of claim 6, further comprising:

a third connection unit configured to connect the first residual gas flow portion of the main block and the second residual gas flow portion of the at least one sub-block.

9. The anesthetic gas distribution device of claim 8, wherein the third connection unit comprises a third flow tube provided in the third connection unit, and the gas, which is introduced into the second residual gas flow portion of the at least one sub-block, flows through the third flow tube.

10. The anesthetic gas distribution device of claim 6, wherein the main block further comprises a gas outlet port connected to the first residual gas flow portion of the main block and configured to discharge the gas, which flows in the first residual gas flow portion of the main block and the second residual gas flow portion of the at least one sub-block, to the outside.

11. The anesthetic gas distribution device of claim 6, further comprising:

a second cover coupled to the second residual gas flow portion of the sub-block positioned at an outermost position from the main block.

12. The anesthetic gas distribution device of claim 1, further comprising:

a first cover coupled to the second passageway portion of the at least one sub-block positioned at an outermost position from the main block.

13. The anesthetic gas distribution device of claim 1, further comprising:

sealing members coupled to sealing member accommodation portions provided on the sliding unit and configured to seal a gap between the first connection unit and the sliding unit and a gap between the second connection unit and the sliding unit.

* * * * *